United States Patent [19]

Meijer et al.

[11] 4,152,331

[45] May 1, 1979

[54] PROCESS FOR THE PREPARATION OF N-SUBSTITUTED 2-PYRROLIDONES

[75] Inventors: Peter J. N. Meijer; Leonardus H. Geurts, both of Geleen, Netherlands

[73] Assignee: Stamicarbon B.V., Geleen, Netherlands

[21] Appl. No.: 898,214

[22] Filed: Apr. 18, 1978

[30] Foreign Application Priority Data

Apr. 18, 1977 [NL] Netherlands ................. 7704179

[51] Int. Cl.² .................................... C07D 207/26
[52] U.S. Cl. .................................... 260/326.5 FL
[58] Field of Search ............ 260/326.5 FL; 326.5 FN

[56] References Cited

U.S. PATENT DOCUMENTS

| | | | |
|---|---|---|---|
| 3,644,402 | 2/1972 | Takagi et al. | 260/326.5 FN |
| 4,036,836 | 7/1977 | Greene | 260/326.5 FN |
| 4,042,599 | 8/1977 | Greene | 260/326.5 FN |

*Primary Examiner*—Jose Tovar
*Attorney, Agent, or Firm*—Cushman, Darby & Cushman

[57] ABSTRACT

A process is described for preparing N-substituted pyrrolidones from succinonitriles by hydrogenation and hydrolysis.

5 Claims, No Drawings

PROCESS FOR THE PREPARATION OF N-SUBSTITUTED 2-PYRROLIDONES

This invention relates to a process for preparing N-substituted 2-pyrrolidones, or such compounds having an alkyl substituent at the 3- and/or 4-carbon atoms, e.g., such as N-methyl-2-pyrrolidone.

Thus, this invention is concerned with an improved method for making compounds of the formula

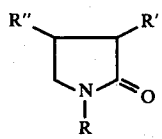

wherein R' and R" independently represent hydrogen or an alkyl group having from 1 to 4 carbon atoms, and R may represent an alkyl group of 1 to 6 carbon atoms or a cycloalkyl group of 5 or 6 carbon atoms.

Such compounds are useful as solvents for polymers, e.g., polyurethanes, or as preferential extracting agents employed in the petroleum industry.

BACKGROUND OF THE INVENTION

In co-pending application Ser. No. 784,367, filed Apr. 4, 1977 now abandoned and Ser. No. 829,781, filed Sept. 1, 1977, now U.S. Pat. No. 4,123,438, granted Oct. 31, 1978, the present applicants have disclosed a method for making unsubstituted 2-pyrrolidones by reacting the same under hydrogenation conditions and at low pressures in the presence of ammonia. That process has not, however, produced N-substituted 2-pyrrolidones.

However, the manufacture of N-substituted 2-pyrrolidones has been investigated elsewhere in the prior art, and there has been an interest in making such compounds as well, and also in improved processes for doing so.

One possible method for the preparation of those pyrrolidones is described in British Patent Specification No. 1,089,083 involving the use of succinic acid, or an alkylsubstituted succinic acid, as starting materials, and converting the same to the cyclic product by reaction with a primary amine. However, this method required prolonged heating, for instance, from 6 to 11 hours, at temperatures of from 200° to 300° C. and at elevated pressures of at least 50 bars and preferably even above 220 bars. Thus, while said to be "simple to operate", in fact such prior art process is at least somewhat less than desirable. Further, such process produces succinimide by-products which require separation from the pyrrolidone products.

DESCRIPTION OF THE INVENTION

It has now been found, in the discovery of the present invention, that instead of succinic acid, or an alkyl-substituted succinic acid, as so used in the prior art, an improved process is achieved by employing the corresponding succinonitrile as the starting material for the preparation of said N-substituted pyrrolidones.

The succinonitriles are actually much cheaper starting materials, than the corresponding acids and their conversion to the pyrrolidone products according to the present invention can be effected in a considerably shorter period of time.

The process according to the present invention for preparing N-substituted 2-pyrrolidones, or 3- and/or 4-alkyl-substituted N-substituted 2-pyrrolidones is therefore particularly characterized by the treatment of the corresponding succinonitrile starting material to hydrogenation in the presence of a primary amine, and then reacting the resulting product with water.

Suitable alkyl-substituted succinonitrile starting materials are especially those succinonitriles substituted with lower alkyl groups having from 1 to 4 carbon atoms, such as mono- or dimethyl succinonitriles. If the starting material is a non-symmetrically-substituted succinonitrile, e.g., a monoalkyl-substituted succinonitrile, the resulting reaction product is a mixture of the N-substituted 3-alkyl and 4-alkyl pyrrolidones.

Various primary amines may be used in this process. Particularly suitable amines are the lower alkyl and cycloalkyl amines having up to six carbon atoms, such as e.g., methyl amine, ethyl amine, propyl amine, etc., and cyclohexyl amine.

A by-product obtained in the process of this invention, in addition to the desired N-substituted pyrrolidone, is the corresponding pyrrolidone lacking the N-substituent, for instance, 2-pyrrolidone itself which is obtained when a non-substituted succinonitrile is used as the starting material. Apparently, two competing reactions are involved in the process. However, the ratio between the amount of N-substituted product and the amount of by-product produced is in turn affected by and can be controlled by the ratio between the amount of the amine and the amount of succinonitrile used in the reaction. When comparatively greater amount of the primary amine is used lesser amounts of said by-product is formed.

The hydrogenation reaction can very ably be effected in the presence of varying amounts of the amine, e.g., from about 0.5 to 50 moles of amine per mole of succinonitrile. If desired, even more than 50 moles of amine per mole of succinonitrile may be used, however, no advantage is thereby realized.

Various temperatures may be employed in the hydrogenation, e.g., temperatures of between about 50° and 250° C. Temperatures of between 80° and 175° C. are preferred as providing the best results.

Further, various partial hydrogen pressures, such as between about 1 and 200 bars, may be used in the hydrogenation. The use of hydrogen pressures above 200 bars is possible in principle, but offers no advantage in practice. Partial hydrogen pressures of between 1 and 100 bars are generally most satisfactory in practice. By preference, the partial hydrogen pressure is kept constant during the hydrogenation, as it is then possible to achieve higher selectivity levels in the reaction.

The water required in this process may be already present during the hydrogenation, so that the conversion into pyrrolidone of the product obtained from the hydrogenation reaction takes place in situ.

Preferably, however, the process is carried out in two separated reaction stages and the water added to the reaction mixture after the hydrogenation reaction, as it is then possible to achieve higher yields. The amount of water so used may vary. Theoretically, 1 mole of water is required per mole of succinonitrile reacted. In practice, a larger amount of water is normally used, e.g., from about 2 to 50 moles per mole of succinonitrile. Use more than 50 moles of water per mole of succinonitrile offers no practical advantage, but may be used, if so desired.

Various temperatures may be employed for the said reaction with water, e.g., between about 25° and 300° C.

Preferably a temperature of between 150° and 250° C. is used, as the reaction will then proceed at a sufficiently rapid rate, while a high yield can moreover be obtained.

The process according to this invention may also be carried either continuously or batch-wise.

For instance, the hydrogenation reaction can very well be effected in the liquid phase by means of hydrogenation catalysts that are known per se, e.g., Raney nickel, nickel boride, Raney cobalt, palladium on carbon, and nickel on silica, etc. Various solvents may also be used in the hydrogenation, such as, e.g., alcohols, alkanes, cycloalkanes, pyridine, pyrrolidone, toluene, benzene, and xylene. The solvent used may also be water, or the primary amine which is itself participating in the reaction during the hydrogenation.

If the reaction with water is effected as a separate step after the hydrogenation, the catalyst may conveniently first be removed after the hydrogenation, e.g., by filtration, and then any solvent which was used in the hydrogenation, may be removed by distillation. If, in this case, a solvent that is immiscible with water is used in the hydrogenation, it offers the advantage that the reaction mixture can be extracted with water after the hydrogenation so that an aqueous phase is formed, which phase can in turn be used for the formation of the pyrrolidone, and the organic phase that is recovered can again be used in the hydrogenation step.

Just as in the hydrogenation reaction, the reaction with water can very well be effected in the liquid state. The desired product, and the by-products, can then be recovered as such by distillation of the final reaction mixture.

If, in a two-step process, the reaction mixture is distilled after the hydrogenation, this distillation is preferably effected under reduced pressure to prevent decomposition of the intermediary product in question.

The process according to this invention is further illustrated by the following Examples, without, however, being limited thereto.

EXAMPLES OF THE INVENTION

EXAMPLE I

Succinonitrile (200 g, 2.5 mols) and toluene (1800 g) are placed in a 5-liter autoclave provided with a stirrer and a heating jacket. The autoclave is closed, after which methyl amine (170 g, 5.47 mols) is fed to the autoclave, and the resulting mixture is heated to 120° C. Next, Raney nickel (20 g) suspended in toluene (50 g) are introduced into the autoclave under pressure and the partial hydrogen pressure is adjusted to 20 bars. After this, the reaction mixture is stirred.

During the reaction hydrogen is fed in to maintain the partial hydrogen pressure at 20 bars. After only about 10 minutes the reaction is completed and the catalyst is removed from the reaction mixture by filtration.

The reaction mixture is then extracted with water (675 g). The aqueous solution thus obtained is heated at 120° C. for 1.5 hours in a closed 5-liter autoclave. After cooling, gaschromatograph analysis of the reaction mixture indicated 58.9 g of N-methyl pyrrolidone had been formed, which is 24% of the theoretically possible yield. In addition, 130 g of 2-pyrrolidone had been formed, which corresponds to 61% of the theoretically possible yield.

That is, total conversion of the nitrile starting material to pyrrolidone products was 85%.

Distillation of the reaction product at 18 mbar produced 56.2 of N-methyl pyrrolidone (b.p. 85° C. at 18 mbar) and 127 g of 2-pyrrolidone (b.p. 138° C. at 18 mbar).

EXAMPLE II

The two-stage procedure of Example I was repeated, but with the use of 390 g (12.56 mols) of methyl amine. In this case, gas-chromatographic analysis of the reaction product showed that 94.7 g of N-methyl pyrrolidone had formed, which is 38% of the theoretically possible yield. In addition, 99.4 g of pyrrolidone had formed, which corresponds to an yield of 47% of the theoretical value. The total yield was thus 85%.

EXAMPLE III

A mixture of succinontrile (200 g, 2.5 mols), methyl amine (293 g, 9.43 mols) and water (2000 g) was heated to 155° C. in a closed autoclave of the type used in Example I. After this temperature has been reached, 30 g of Raney nickel suspended in 30 g of water was forced into the autoclave by means of hydrogen, and the partial hydrogen pressure was adjusted to 30 bars. The mixture was stirred at this temperature for 4 hours, while maintaining the partial hydrogen pressure at 30 bars by additional supply of hydrogen.

After completion of this single stage reaction, the catalyst was separated from the reaction mixture by filtration, the reaction mixture cooled to room temperature and analyzed gas-chromatographically. 44.5 grams of N-methyl pyrrolidone are found to have formed, which is about 18% of the theoretically possible yield. In addition, 25.5 grams of pyrrolidone were detected, which corresponds to an yield of 12% of the theoretical value.

EXAMPLE IV

Example I was repeated under the same conditions, but with the use of cyclohexyl amine (2000 g) instead of toluene and methyl amine. After the hydrogenation, 850 g of water was added and the hydrolysis reaction was effected as described in Example I.

Gas-chromatographic analysis of the reaction mixture showed the production of 39.3 g of N-cyclohexyl pyrrolidone corresponding to an yield of 9.5% of theoretical, and in addition, 106.3 g of 2-pyrrolidone were formed, corresponding to 50% of the theoretically possible yield.

The procedures of the foregoing Examples may also be employed with mono- or di-alkyl-substituted succinonitriles and with other amines, with desirable results as described above.

What is claimed is:

1. A process for preparing N-substituted compounds of the formula

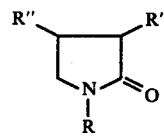

wherein R' and R" independently represent hydrogen or an alkyl group having from 1 to 4 carbon atoms, and R may represent an alkyl group of 1 to 6 carbon atoms or a cycloalkyl group of 5 or 6 carbon atoms which comprises subjecting a succinonitrile of the formula

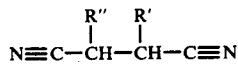

to hydrogenation in the presence of a primary amine of the formula R—NH$_2$, at a temperature between about 50° C. and 250° C. and under a partial hydrogen pressure of between 1 and 200 bars, and followed by hydrolysis of the hydrogenated product with water.

2. The process of claim 1 wherein said hydrogenation and said hydrolysis are effected in two separated reaction stages.

3. The process of claim 1 wherein said hydrolysis is carried out at a temperature between about 25° C. and 300° C.

4. The process of claim 1 wherein from 2 to 50 mols of water are present per mol of succinonitrile starting material.

5. The process of claim 1 wherein from 0.5 to 50 mols of said amine are used per mol of succinonitrile starting material.